(12) United States Patent
Pierce

(10) Patent No.: US 7,351,544 B2
(45) Date of Patent: Apr. 1, 2008

(54) METHODS TO IDENTIFY AND QUANTIFY OLIGOSACCHARIDE MODIFICATIONS OF GLYCOPROTEINS

(75) Inventor: J. Michael Pierce, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 56 days.

(21) Appl. No.: 11/223,323

(22) Filed: Sep. 8, 2005

(65) Prior Publication Data

US 2006/0078920 A1  Apr. 13, 2006

Related U.S. Application Data

(60) Provisional application No. 60/607,951, filed on Sep. 8, 2004.

(51) Int. Cl.
*G01N 33/53* (2006.01)
*C12Q 1/68* (2006.01)
*C12P 19/34* (2006.01)

(52) U.S. Cl. .......................... 435/7.1; 435/6; 435/91.2

(58) Field of Classification Search ..................... None
See application file for complete search history.

*Primary Examiner*—James Martinell
(74) *Attorney, Agent, or Firm*—Arnall Golden Gregory LLP; Clark G. Sullivan

(57) ABSTRACT

Methods are disclosed for identifying oligosaccharides found on proteins and identifying those that are modified in disease states.

27 Claims, No Drawings

METHODS TO IDENTIFY AND QUANTIFY OLIGOSACCHARIDE MODIFICATIONS OF GLYCOPROTEINS

RELATION TO PRIOR APPLICATIONS

The present application claims priority to U.S. Ser. No. 60/607,951, filed Sep. 8, 2004, the contents of which are hereby incorporated by reference.

FIELD OF THE INVENTION

The present invention relates to methods for identifying oligosaccharides found on proteins and identifying those that are modified in disease states.

BACKGROUND OF THE INVENTION

Early diagnosis is one of the primary determinants of mortality and morbidity from disease. The recognition of a variety of diseases, notably cancers, in apparently healthy subjects and subsequent treatment thereof is still problematic. Alterations in post-translational modifications of readily attainable samples from patients is the best indicator of the disease state, although most potential markers are as yet unknown. Current diagnostic tests are often inaccurate and invasive. For example in the case of the commonly used cancer marker prostate specific antigen, levels of normal expression vary dramatically between individuals, and current tests are only beginning to address this issue (See U.S. Pat. No. 6,261,791).

The covalent attachment of oligosaccharides to protein is the most common post-translational event and occurs in more than 50% of proteins, independent of membrane linkage. Glycosylation occurs at specific locations along the polypeptide backbone of the protein. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be any amino acid except proline. N-acetylneuramic acid (also known as sialyl acid) is usually the terminal residue of both N-linked and O-linked oligosaccharides. Variables such as protein structure and cell type influence the number and nature of the carbohydrate units within the chains at different glycosylation sites. Glycosylation isomers are also common at the same site within a given cell type. The levels of glycosylation are a reflection of the levels and activities of different glycosyltransferases and glycosidases responsible for the intracellular construction of oligosaccharides.

There is now overwhelming evidence that glycosylation of glycoproteins is markedly altered in diseased cells (see for example Dwek et al., 2001; Hanisch, 2001; Hakomori, 2002). Altered glycosylation is a common feature in the transformation to malignancy of certain cancers and has been related to the invasiveness and metastatic potential of tumor cell lines. Studies have shown that variations in glycosylation have the potential to be used as diagnostic tools for disease states, in particular for cancers. Carbohydrate profiles of primary tumors have been correlated with tumor grade, metastatic potential, and disease prognosis (Litynska, et al., Melanoma Rsch., 2001, 205-212; Hakomori, S., 1989, Adv. Cancer Res., 52:257-331).

A number of studies have attempted to identify specific glycoproteins that are altered in disease states, in particular to recognize markers of cancer. In many of these studies, cell or tissue extracts were separated and probed using one or more lectins that were conjugated for visualization. The levels of binding of the lectin could thereafter be compared between tumor and control cells to identify protein bands with altered levels of glycosylation that could subsequently be excised for sequencing. However, traditional techniques for protein separation, such as 2D-electrophoresis are technically limiting in that only about 20% of the proteins loaded on a 2D-electrophoresis gel are visible, and of those, only the proteins with masses ranging between 10 kDa and 100 kDa are readily separated. In addition, relevant expression differences are difficult to confirm since multiple gels are difficult to prepare in a reproducible manner. Additional techniques to identify variations in glycosylations utilizing the affinity of glycoproteins to subsets of lectins include serial lectin-affinity chromatography (for example Endo, 1996, J. of Chromatography. A 720(1-2):251-61). Sequential chromatography steps using several lectins with different binding properties are used to purify a subset of glycoproteins. Subsequent identification techniques for either method usually involve proteolysis and mass spectroscopy. These methods are both time consuming and costly. Current techniques therefore can only detect a subset of available glycoproteins, have limited sensitivity to low levels of proteins, and are not quantitative. These methods also do not allow direct identification of glycosylated residues on specific molecules. Thus, there exists a need for convenient and efficient methods to analyze a large array of proteins and modifications thereof for the development of diagnostic devices.

Almost all glycoproteins exhibit polymorphism associated with their glycan moieties. This type of diversity is termed microheterogeneity and these different forms have been termed "glycoforms". These variants were first characterized in the alpha1-acid glycoprotein (AAG) from human serum by Schmid et al (1962, Biochemistry J. 1:959). The microheterogeneity was found to be due to the occurrence of di-, tri-, and tetra-antennary glycans at the glycosylation sites. Much variability occurs in the regulation of later stage processing of N-linked glycosylations. N-linked glycosylation is initiated by the transfer of an oligosaccharide to asparagine residues of newly synthesized proteins. Subsequent modification of this oligosaccharide by Golgi enzymes (Hsieh, P., et al., 1983, J. Biol. Chem., 258:2555-2561) generates the extreme diversity of N-linked oligosaccharides found in mature glycoproteins. However, the regulation of these later stages of processing is only poorly understood. Microheterogeneity of oligosaccharide modifications is wide-spread and has been seen in a number of glycoproteins, including those found in disease states. For example, branching of N-linked oligosaccharides is increased in a number of differentiated and oncogenically transformed cells (Feizi, T., 1985, Nature, 314:53-57; Yamashita, K., et al., 1984, J. Biol. Chem., 259:10834-10840; Warren, L., et al., 1978, Biochem. Biophys. Acta., 516:97-127), as well as in metastases of murine melanomas and fibrosarcomas (Dennis, J. W., et al., 1987, Science, 236:582-585). This is likely to have physiologically significant consequences, since altered protein glycosylation can affect processes such as adhesion, metastasis and immune recognition. (Hubbard, S. C., 1987, Journal of Biological Chemistry, 262 (34):16403-16411). Because there is reason to believe that the variations of oligosaccharide modifications in disease states may correspond to distinct markers of disease on particular proteins of interest, a method that can easily identify and quantify this variability will provide a novel and valuable diagnostic tool.

Currently, most glycosylation sites are unknown and glycoprotein prediction is dependent on in silico prediction, rather than substantiated experimentation. In fact, more than 90% of glycosylation data in the *C. elgans* proteome database is based on in silico prediction (Hirabayashi, J., 2002, J. Chromatogr. B 771:67-87). Therefore, there exists a need for a method that could identify particular sites of oligosaccharide modification on individual proteins to provide valuable information to the research community.

Methods exist to purify separated carbohydrates, or separated glycoamino acids from glycoproteins to allow their identification (see for example U.S. Pat. No. 6,077,951). These methods can furnish useful information to allow identification of disease markers, however they are time consuming. To identify any particular glycosylation sites associated with an oligosaccharide moiety, multiple purification steps are required and these steps can limit the glycoproteins from which information could be gathered.

A more relevant method to identify glycosylation sites is disclosed in E.P. 1,008,852A1. This reference discloses a technique to identify specific glycoproteins using an immobilized binding agent which binds to either a sugar or a peptide sequence and a second, non-immobilized but easily identified binding partner which recognizes the other aspect of the glycoprotein (either the sugar or peptide). This technique, while a step forward in that it allows identification of modifications on specific proteins, is still limited in the detection levels that it allows. In addition, the analysis of multiple glycosylation sites or multiple peptides can become time consuming. A need clearly exists for more sensitive assays that can be used to identify modifications on proteins of interest and detect low levels of diagnostic analytes in solution Building on the idea of analyzing proteins using multiple binding partners, E.P. 0,832,431B1 discloses a method to quantify proteins captured from solution using three binding agents: one to stabilize the protein and two to detect specific epitopes. In this reference oligonucleotides are linked to the specific recogntion agents and the binding of these molecules is recognized by amplification of the oligonucleotides (as described in U.S. 2002/0,051,974A1). In most cases these techniques are limited in that they only identify a particular epitope in a sample, they do not give structural information, nor do they differentiate between multiple forms of a target. Moreover, assays that use antibodies as capture agents have detection limits that are approximately 1% of the antibody Kd (1 picogram/ml for the highest affinity antibodies). The method described in E.P. 0,832,431B1 is clearly an improvement on previous techniques, in that it provides the possibility of detecting very small quantities of protein, however, it still requires additional washing steps, and because of the requirement for immobilizing an antigen, would only be useful for a restricted array of molecules since many may not bind properly. In addition, this method limits the possible analysis of post-translational modifications because the immobilization step can mask specific binding regions, in particular carbohydrate moieties. To overcome some of these difficulties, U.S. 2002/0,064,779A1 (also see Fredriksson et al., Nature Biotech. 20:473-477, 2002) discloses a method for identifying analytes in solution using a similar proximity based assay. This reference suggests that non-peptide modifications could be analyzed using this technique, however the method is not applied towards the detection of specific glycoproteins in solution, nor is it targeted towards classifying glycan heterogeneity in disease states.

Therefore, despite these advances, a need continues to exist for a method with improved sensitivity, improved range and requiring less manipulation to more rapidly analyze samples for the presence of and for the amount of target glycoproteins. There is additionally a need for an efficient method to discriminate the oligosaccharide modifications on proteins of interest from a population of proteins and to quantify said modifications, for the purpose of developing diagnostic tools to efficiently screen individuals for diseases such as cancer.

OBJECTS OF THE INVENTION

Accordingly, it is an object of the present invention to provide an efficient method to characterize the array of oligosaccharides attached to specified glycoproteins.

It is a further object of the present invention to quantify the carbohydrate attachments on glycoproteins of interest from native samples.

It is a further object of the present invention to identify a set of proteins from native samples that contain specified glycan structures of interest.

It is still a further object of the present invention to identify and quantify the heterogeneity of carbohydrate groups attached to a glycoprotein of interest.

A further object of the present invention is to identify the position of specified oligosaccharide modifications on a specified protein.

Another object of the present invention is to provide a method to identify the oligosaccharide modifications on proteins from cell samples that can act as disease markers.

Another object of the present invention is to provide methods to identifying glycoproteins that can act as disease markers because they are differentially glycosylated in diseases.

Yet another object of the present invention is to provide methods for identifying glycoproteins that can act as disease markers because they are differentially expressed in diseases versus non-diseases cells.

SUMMARY OF THE INVENTION

These and other objects are achieved by methods to identify the proximity of recognition agents for multiple features of a protein, including known and speculative carbohydrate and peptide sequences and structures, thereby identifying the carbohydrate moieties attached to specific sites on glycoproteins. The invention provides an efficient method to identify and quantify carbohydrate modifications on proteins by eliminating the additional steps of binding proteins to a solid support or separating bound molecules.

The invention provides a method to detect oligosaccharide sequences on glycoproteins of interest by analyzing the proximity of agents that bind selectively to either carbohydrate or peptide aspects of a glycoprotein. This method is generally performed by a) providing a glycoprotein; b) contacting a first agent for recognizing an oligosaccharide and a second agent for recognizing a peptide to said glycoprotein; and c) detecting proximity of said first and second recognition agents. The glycoprotein in this case acts analogous to a catalyst by bringing the reactive probes closer to one another and increasing their capacity to interact by increasing their local concentration. The proximity of the two recognition agents results in a detectable signal in a secondary reaction.

In one embodiment, the recognition agents are linked to variable length oligonucleotides with non-complementary sequences. The proximity of the recognition agents can be measured by contacting the two oligonucleotide sequences with a third oligonucleotide which is in part complementary to the first, and in another part complementary to the second of the oligonucleotides linked to the detecting agents. The third oligonucleotide, defined as a "linker", will bind to the first two due to the affinity of these complementary sequences. The first two sequences will therefore be forced into close proximity and can thereafter be ligated to one another. The detection can be carried out using any amplification reaction which will amplify only the ligated product and not the individual oligonucleotides. These reactions include, but are not limited to, variations of the polymerase chain reaction (PCR), strand displacement amplification (Nadeau J G, 1999, Amplification.Anal Biochem 276(2): 177-187), NASBA (van Deursen P B, 1999, Nucleic Acids Res;27(17):e 15), RNA transcription (White S R, et al., 1999, Nucleic Acids Res;27(19):e25), or invader assay (Kwiatkowski R W, et al, 1999, Mol Diagn;4(4):353-364). The amplification reaction can be followed in real-time using any available method. In the preferred embodiment, the amplification is measured using real-time PCR with one nucleotide primer complementary to a sequence found exclusively in the first oligonucleotide and another nucleotide primer complementary to a sequence found exclusively in the second oligonucleotide. The real-time PCR assay utilizes standard techniques well known in the art. Using the real-time PCR amplification it is possible to quantify glycan modifications on glycoproteins of interest.

Another aspect of the invention does not require a linker oligonucleotide, but takes advantage of the fact that nucleic acids will oligomerize by phosphodiester bonding in a concentration dependent manner in the presence of a ligating enzyme. The recognition agents and linked oligonucleotides are therefore added to sample at a concentration so low that the oligonucleotides will not react with each other to any great extent unless the recognition agents are bound to the analyte, in which case the higher local concentration promotes interaction between the probes. In the preferred embodiment of this invention, one of the recognition agents will have a oligonucleotide coupled to it by its 5' end while the other recognition agent has a second oligonucleotide coupled to it by its 3' end. The first oligonucleotide thus has a free 3' hydroxyl capable of reacting with the 5' phosphate of the second nucleotide sequence. This embodiment is advantageous in the fact that it does not require an additional nucleotide moiety and will display very low background.

The methods of this invention can be used to analyze a number of characteristics of glycoprotein glycosylation which current techniques are unable to do efficiently. For example, in one embodiment of the invention, the site of interaction of the second, peptide recognition agent is known and the length of any of the oligonucleotides is varied incrementally in sequential assays. Based on the analysis of the results of these assays, a determination of the localization of the binding site of the first recognition agent (ie. the location of the glycan moiety) can be inferred based on the known or surmised three-dimensional structure of the protein.

In another embodiment of the invention, the first recognition agent detects a variety of carbohydrate moieties, while the second recognition agent detects a peptide sequence. This aspect can detail the multiplicity of carbohydrate modifications on specified proteins, which are likely to vary depending on disease states. In a separate embodiment of this invention, the first agent is specific for a subset of carbohydrate moieties while the second agent comprises a set of peptide binding agents, for example a library of aptamers. In this embodiment the invention will classify those proteins with a particular set of carbohydrate moieties.

Each of these inventions can be used to analyze proteins found in samples from a variety of disease states including, but not limited to, serum from cancer patients. The samples can be any form of tissue or cell, or any lysate thereof. The invention further embodies comparing the glycosylation of proteins from diseased samples to control samples, thereby identifying target proteins which are altered in disease states. One of the many advantages of this invention is that there is no requirement for serial purification steps, causing less loss of protein and decreasing cost and time required to develop and potentially utilize diagnostic data.

Thus, the present invention furthers our understanding of how cells regulate post-translational modifications and additionally allows the identification of diagnostic markers that will provide a basis for the development of non-invasive diagnostic tests. These methods are more fully described and exemplified below.

DETAILED DESCRIPTION OF THE INVENTION

In one embodiment, the present invention provides for a method of detecting oligosaccharide sequences on glycoproteins of interest comprising a) providing a glycoprotein; b) contacting a first recognition agent for detecting an oligosaccharide and a second recognition agent for detecting a peptide to said glycoprotein; and c) detecting the proximity of said recognition agents.

Providing a Glycoprotein

The glycoprotein of interest can be provided either in isolation or in a sample of high complexity, such as serum. In one embodiment of the invention, the glycoprotein of interest is found in a complex solution. In one preferred embodiment, the complex solution is serum from humans. In a separate preferred embodiment, the complex solution in which the glycoprotein of interest is found comprises solubilized cells. Suitable tissues from which cells are derived are blood, muscle, nerve, brain, heart, lung, liver, pancreas, spleen, thymus, esophagus, stomach, intestine, kidney, testis, ovary, skin, bone, breast, uterus, bladder, spinal cord, or various kinds of body fluids. The cells may also differ in developmental stage, as well as developmental origin such as ecotodermal, mesodermal, and ectodermal origin.

In a further preferred embodiment, the serum is derived from patients with a disease for which there is a basis to expect to identify glycoprotein markers. It will be appreciated that the present invention can be used to study glycosylation of proteins in a wide variety of disease states. In a preferred embodiment the invention will be used to identify proteins from diseased cells that display aberrant glycosylation patterns when compared to non-diseased cells.

In one preferred embodiment of the invention, cells or serum taken from mammals with hyperpoliferative disorders are used. Examples of hyperpoliferative disorders for which disease markers can be investigated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract, Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphorria, Adult Lymphocytic Leukemia, Adult Non-Hodgkin's Lymphoma, Adult Primary Liver Cancer, Adult Soft Tissue Sarcoma, AIDS-Related Lymphorria, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System Primary) Lymphoma, Central Nervous System Lymphorria, Cerebellar Astrocytoma, Cerebral Astrocytoma, Cervical Cancer, Childhood (Primary) Hepatocellular Cancer, Childhood Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalanic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancer, Esophageal Cancer, Ewing's Sarcoma and Related Tumors, Exocrine Pancreatic Cancer, Extraeranial Germ Cell Tumor, Extragonadal Germ Cell Tumor, Extrahepatie Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyrigeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethial Cancer, Uterine Cancer, Uterine Sarcoma, Vaginal Cancer, Visual Pathway and Hypothalarruc Glioma, Vulvar Cancer, Waldenstroin's Macroglobulinemia, Wilm's Tumor, and any other hyperproliferative disease located in an organ system listed above. Hyperplastic disorders for which diagnostic markers can be developed include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

In another embodiment the invention is employed to identify markers of premalignant conditions known or suspected of preceding progression to neoplasia or cancer, in particular, where non-neoplastic cell growth is consisting of hyperplasia, metaplasia, or most particularly, dysplasia has occurred (for review of such abnormal growth conditions, see Robbins and Angell, 1976). In one aspect of the invention, glycoproteins from samples of tissue or serum from mammlas harboring disease at different stages are analyzed. This provides for a method to identify prognosis markers for individual diseases.

Additional conditions for which glycosylation can be investigated using the methods of the present invention include but are not limited to, progression, and/or metastases of malignancies and related disorders such as leukemia (including acute leukemia (e.g., acute lymphocytic leukemia, acute myelocytic leukemia (including myeloblastic, promyelocytic, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, Sarcomas and, carcinomas such as fibrosarcoma, myxosarcoma, fiposarcoma, chondrosarcoma, osteogenic sarcoma, chordoma, anglosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

Although tumors are the best example of diseases in which protein glycosylation is known to be dramatically altered, any other cell for which there is a reason to desire the identification of glycan moieties on known proteins or the identification of glycoproteins can be used. In another embodiment of the invention, cells or serum taken from patients or from a model organism harboring diseases other than cancer can also be used to identify differences in protein glycosylation. These diseases include muscular dystrophy (Michele et al., 2002; Moore et al., 2002), diabetic microvascular complications, and cystic fibrosis (Scanlin and Glick, 2001).

In another embodiment, cells harboring diseases including autoimmune disorders (such as, multiple sclerosis, Sjogren's syndrome, Hashimoto's thyroiditis, biliary cirrhosis, Behcet's disease, Crohn's disease, polymyosifis, systemic lupus erythematosus and immune-related glomeruionephritis and rheumatoid arthritis) and viral infections (such as herpes viruses, pox viruses and adenoviruses), inflammation, graft v. host disease, acute graft rejection, and chronic graft rejection are used for study.

Diseases associated with increased apoptosis, which are also likely to exhibit specific glycan variations include AIDS; neurodegenerative disorders (such as Alzheimer's disease, Parkinson's disease, amyotrophic lateral sclerosis, retinitis pigmentosa, cerebral degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemiclupus erythematosus and immune-related glomerulonephritis and rheumatoid arthritis) myelodysplastic syndromes (such as a plastic anemia), graft Y host disease, ischemic injury (such as that caused by myocardial infarction, stroke and repercussion injury), liver injury (e.g., hepatitis related liver injury, ischemia/Eeperfusion injury, cholestosis (bile duct injury) and liver cancer); toxin-induced liver disease (such as that caused by alcohol), septic shock, cachexia and anorexia.

In addition, because immortal mammalian tumor cell lines recapitulate many of the features of the parent cells they were developed from, including regulated glycosylation, one embodiment of this invention analyzes immortalized tumor cell lines for potentially secreted glycoproteins. In addition, this method can be applied to hyperproliferative disorders (described above), which have been exposed to chemotherapeutic agents. In another embodiment, the disorders associated with increased apoptosis (such as AIDS; neurodegenerative disorders; autoimmune disorders, myelodysplastic syndromes, graft Y host disease, ischemic injury, liver injury, toxin-induced liver disease, septic shock, and cachexia) can be analyzed after treatment. These embodiments have the potential to identify markers indicating relapse or remission in patients who have undergone treatment.

In a separate embodiment of the invention, the sites of glycosylation on proteins developed from either recombinant or native sources can be analyzed. In a specific embodiment of the invention, the conformation of glycoprotein glycans can be identified on purified proteins. Proteins purified from lysates of either eukaryotic or prokaryotic cells can be used for this purpose. In a further specific embodiment of theis invention, the efficiency of deglycosylation of purified glycoproteins can be analyzed fro research purposes. One application of this embodiment is the analysis of novel deglycosylation techniques. In a further application of this invention, the efficiency of glycoprotein separation techniques for research purposes can be analyzed by testing the proportion of glycoprotein separated from the initial mixture.

Carbohydrate Binding Agents

In one embodiment of this invention, the oligosaccharide recognition agent comprises one or more lectins. Lectins are herein defined as a sugar-binding protein of non-immune origin that can precipitate glycoconjugates and contain at least one sugar-binding sites. The structural information obtained from a large number of mammalian lectins has led to their classification into several families which exhibit a number of variable properties, including ion dependence and solubility (see for example, Drickamer, K., J. Biol. Chem., 1988, 263: 9557; Drickamer, K., Curr. Opin. Struc. Biol., 1993, 3: 393; Drickamer, K., Biochemical Society Transactions, 1993, 21: 456). In addition, certain lectins bind DNA molecules, depending on conditions (see Vieira-Breitwieser O, $20^{th}$ Annual International Lectin Meeting Abstracts, T25, 2002), therefore the conditions of the assay will vary depending on the lectin used. The lectins that can be used in this application include those derived from the group consisting of animal derived, galactose-binding lectins (termed Galectins); Ca-dependent (C-type) animal lectins including sialyl-Lewis X recognizing selectins and mannose-specific collectins; glycosaminoglycan binding annexins; plant-derived lectins including concanavalin A, and ricin, and invertebrate lectins such as tachylectins or *Xenopus* oocyte lectins.

The choice of lectin will dictate the subpopulation of glycoproteins that are analyzed in each iteration. Thus, in preferred embodiments, lectins that are known to recognize carbohydrate moieties that are altered in disease states are used. In further preferred embodiments, the lectins used include β1-6 oligosaccharide binding leukoagglutinin (L-PHA), Concanavalin A (ConA), which has affinity for oligomannosyl saccharides found in N-glycans, galectins including Galectin LEC-6, specific for LacNAc-containing glycans, *Aleuria aurantia* lectin (AAL) with broad specificity for L-Fuc-containing oligosaccharides, Peanut agglutinin (PNA), which is specific for Galβ1-3GalNAc), found widely in O-glycans, and *Helix pomatia* lectin (HPA), which binds N-acetylgalactosamine.

In addition to conjugated lectins, other non-lectin sugar binding proteins including sugar-specific enzymes and transport proteins can be used in this method. Mono- or poly-clonal antibodies specific to one or more carbohydrate moieties may be used. These can include antibodies that are commercially available, such as Anti-blood Group A Isotypes; Anti-blood Group B Isotype; Anti-blood Group H Isotypes; Anti-Le Isotypes; Anti-GM3 Isotypes; Anti-E-selectin Isotypes; Anti-MUC1 Isotypes; Anti-Extended sialyl-Lewis Isotypes Anti-Gb3 Isotypes.

In addition to agents that bind carbohydrate moieties, specific glycoproteins found on the extracellular leaflet of cells or in serum can be analyzed by reagents that recognize the inositol 1,2-cyclic monophosphate moiety released by phospholipase cleavage of a GPI anchored proteins, which has been referred to as the cross-reacting determinant (CRD). This moiety can be readily detected by antibodies that are either commercially available or independently developed by techniques well known in the art.

Boronic acids that are specific for saccharide moieties have also been developed that would be suitable for use in the present invention. For example, phenylboronic acid is known to prefer D-fructose to D-glucose, sucrose and D-galactose. Lorand et al., J. Org. Chem., 1959, 24, 769. James et al., Topics in Curr. Chem., 2002, 218, 159, report the CD spectral data and association constants of different saccharides with diboronic acid. Phenylboronic acid is also known to bind to catechol type of compounds more tightly than most aliphatic diols. These properties have been exploited to prepare boronic acid-based sensors based fluorescence, color and ultraviolet sensing, absorption spectroscopy, and electrochemical detection that can be exploited in the practice of this invention. Wang et al., Current Organic Chem., 2002, Vol. 6, No. 14. Improvements in the selective recognition of these systems can be improved by, for example, adding additional boronic acid binding site(s) to recognize a second pair of diols or other recognition moieties. A carefully built scaffold with two or more boronic acids in spatial arrangement that is complementary to the target saccharide should be able to bind to that saccharide with high affinity and binding specificity.

Peptide Binding Agents

In one aspect of this invention, the second recognition agent detects a peptide sequence. In a further embodiment, the second recognition agent detects a three-dimensional peptide structure, which may be made up of non-adjacent amino acids and may optionally depend on the addition of further post-translational modifications. Recognition agents with a dissociation constant ($K_D$) of less than about $10^{-6}$ are preferred. The recognition agent can be chosen from any of a variety of reagents including antibodies, aptamers, or other peptide interacting reagents. The agent may optionally be a naturally occurring, recombinant, or synthetic biomolecule. Antibodies or antibody fragments are highly suitable as protein-capture agents. Antigens may also serve as recognition agents, since they are capable of binding antibodies. A receptor which binds a protein ligand is another example of a possible agent. Agents are also not to be limited to agents which only interact with their binding partners through noncovalent interactions. Either peptide or oligosaccharide recognition agents may also optionally become covalently attached to proteins which they bind. For instance, the agent may be photocrosslinked to its binding partner following binding.

Antibodies

In one embodiment of the invention, either the oligosaccharide recognition agent or the peptide recognition agent or both recognition agents comprise at least one antibody. As used herein, the term "antibody" is used in its broadest sense to include polyclonal and monoclonal antibodies, as well as antigen binding fragments of such antibodies. An antibody useful in the invention, or antigen binding fragment of such an antibody, is characterized by having specific binding activity for a ligand or sample epitope. Thus, Fab, F(ab')$_2$, Fd, Fv, single chain Fv (scfv) fragments of an antibody and the like, which retain specific binding activity for a ligand, are included within the definition of an antibody. Specific binding activity of an antibody for a ligand can be readily determined by one skilled in the art, for example, by comparing the binding activity of an antibody to a particular ligand versus a control ligand that differs from the particular ligand. Specific binding can similarly be determined for a recognition agent that is not an antibody.

Both naturally occurring as well as non-naturally occurring antibodies may be utilized as recognition agents in this invention, including, for example, single chain antibodies, chimeric, bifunctional and humanized antibodies, as well as antigen-binding fragments thereof. Methods of preparing polyclonal or monoclonal antibodies are well known to those skilled in the art (see, for example, Harlow and Lane, 1988, Antibodies: A Laboratory Manual). Non-naturally occurring antibodies can be constructed using solid phase peptide synthesis, can be produced recombinantly or can be obtained, for example, by screening combinatorial libraries consisting of variable heavy chains and variable light chains as described by Huse et al. (1989, Science 246:1275-1281; Kang et al., 1991, Proc. Natl. Acad. Sci. USA, 88:4363-4366). The advantage of using such a combinatorial antibody library is that antibodies do not have to be individually generated for each ligand. These and other methods of making functional antibodies are well known to those skilled in the art (Winter and Harris, 1993, Immunol. Today 14:243-246; Ward et al., 1989; Nature 341:544-546; Hilyard et al., 1992, Protein Engineering: A practical approach; Borrabeck, 1995, Antibody Engineering, 2d ed.).

Any known method for identifying and selecting antibodies, fragments or derivatives thereof can be used. For example in that these can be detected after appropriate labeling when they have bound to isolated or purified antigen, or by immunoprecipitation of the antigen which has been purified, for example, on polyacrylamide gels, or by antibodies against the blood group antigens competing with other blood group-specific antibodies for binding to sugar side chains.

In one embodiment, the antigen recognition agent is a monoclonal antibody specific for a peptide sequence near a site of Asn-linked glycosylation or near a site of Ser-O-glycosylation. In one embodiment, the glycan recognition agent is a monoclonal antibody specific for a glycan sequence or a glycan structure.

Buffer Conditions

The binding of the first and second recognition agents may depend on the conditions of the sample. For example, in one embodiment, tissues are solubilized in one or more detergents. If in this embodiment the first or second recognition agents are antibodies, the buffer may require dilution to reduce the detergent concentration to favor interaction of the antibody with the epitope to which it binds. In preferred embodiments, conditions used favor protein binding. The conditions that are variable include pH, salt concentration, detergent concentration and detergent identity, protein concentration, and temperature.

Aptamers

In preferred embodiments of the present invention, either the first recognition agent, the second recognition agent or both recognition agents are one or more aptamers. "Aptamers" are herein defined as nucleic acid molecules that are selected from random or high-sequence diversity libraries due to their ability to bind with a target. They are relatively small (8 kDa to 15 kDa) synthetic compounds that can be selected to possess high affinity and specificity for target molecules. Aptamers embody both the affinity properties of monoclonal antibodies and single chain antibodies and the manufacturing ease at least as efficient as that of a small peptide.

Aptamers can be generated by in vitro screening of complex nucleic-acid based combinatorial shape libraries ($>10^{14}$ shapes per library) employing a process termed SELEX (for Systematic Evolution of Ligands by Exponential Enrichment) (Tuerk et al, Science 249:505-10 (1990)). The SELEX process consists of iterative rounds of affinity purification and amplification of oligonucleotides from combinatorial libraries to yield high affinity and high specificity ligands. Combinatorial libraries employed in SELEX can be front-loaded with 2' modified RNA nucleotides (e.g., 2'fluoro-pyrimidines) such that the aptamers generated are highly resistant to nuclease-mediated degradation and amenable to immediate activity screening in cell culture or bodily fluids. An iterative process is used to enrich the library for species with high affinity to the target. The iterative process involves incubation of the library with the target, separation of target bound oligonucleotide ("TBO") sequences from free TBO and amplification of the bound and thus selected TBO population to enrich the library. Amplification may be effected enzymatically, for example, using a thermostable DNA polymerase in a polymerase chain reaction ("PCR"). The result is a sub-library populated with a small subset of sequences that have a high affinity for the target. The library is then subcloned to sample and preserve the target specific DNA, RNA or mixed sequences selected. These compounds may then be studied in further detail to elucidate the mechanisms by which they interact with the target.

Several methods have been developed that modify the base SELEX process to obtain aptamers that satisfy objectives in addition to exhibiting high binding affinity toward a target molecule. For example, a number of patents disclose the use of modified nucleotides in the SELEX process to obtain aptamers that exhibit improves properties. U.S. Pat. No. 5,660,985, for example, claims SELEX using 2'-modified nucleotides that display enhanced in vivo stability. U.S. Pat. No. 6,083,696 discloses a "blended" SELEX process in which oligonucleotides covalently linked to non-nucleic acid functional units are screened for their capacity to bind a target molecule. Other patents describe post-SELEX modifications to aptamers to decrease their size, increase their stability, or increase target binding affinity. See, e.g., U.S. Pat. No. 5,817,785 and U.S. Pat. No. 5,648,214.

Although the invention is targeted towards reducing non-specific recognition of carbohydrate and protein conjugates, recognition agents may still bind non-specifically to analytes, particularly in preferred embodiments in which glycoproteins are analyzed in samples of high complexity. In the event that non-specific reactant products are formed, blocking reagents may be added to the sample to limit this interaction. These blocking reagents may include, but are not limited to, reagents such as serum or serum derivatives such as albumin, small peptides or antibodies.

In one embodiment, the peptide and glycan recognition agents both monoclonal antibodies. In one sub-embodiment, the peptide and glycan recognition, antibodies are deglycosylated. In a further embodiment, the antibodies are cleaved to remove the glycan moiety on the constant region. These cleaved antibodies may be recombined, providing a dual recognition, hybrid antibody. The dual-recognition antibody may be further modified with an oligonucleotide.

There are several known methods to deglycosylate antibodies, including both enzymatic and chemical procedures (Hobbs S M., et al. *Molecular Immunology.* 29(7-8):949-56, 1992; Kottgen, et al., (*Biol. Chem. Hoppe-Seyler,* 369:1157-1166 (October 1988). Antibody fragmentation by enzymes is known. The enzymes known include pepsin, papain, and ficin. Some references indicate that cleaved antibody fragments do not exhibit all the same properties as antibody fragments developed by recombinant means (see for e.g. U.S. Pat. No. 4,937,183). Many studies have shown that antibody fragments produced by recombinant means (i.e. by producing isolated fragments from recombinant DNA) can be used to detect antigens in samples and can be utilized to detect antigens by linking the fragment to a matrix (described in: Oelschlaeger, et al. *Analytical Biochemistry.* 309(1):27 (2002); Ramirez N., et al. *Transgenic Research.* 11(1):61-4 (2002); Hock B., et al. *Biosensors & Bioelectronics.* 17(3):239-49 (2002); Foy B D., et al. *Journal of Immunological Methods.* 261(1-2):73-83 (2002); Battersby J E., et al. *Journal of Chromatography. A.* 927(1-2):61-76 (2001); Stausbol-Gron B., et al. *European Journal of Biochemistry.* 268(10):3099-107 (2001); Schmiedl A., et al. *Protein Engineering.* 13(10):725-34 (2000); Schmiedl A., et al. *Journal of Immunological Methods.* 242(1-2):101-14 (2000); Horn I R., et al. *FEBS Letters.* 463(1-2):115-20 (1999); Grant S D., et al. *Journal of Agricultural & Food Chemistry.* 47(1):340-5 (1999); Sanchez L., et al. *Journal of Biotechnology.* 72(1-2):13-20 (1999); Casalvilla R., et al. *Journal of Biotechnology.* 72(1-2):1-12 (1999); Hengerer A., et al. *Biotechniques.* 26(5):956-60, 962, 964 (1999); Reinhold U., et al. *Journal of Investigative Dermatology.* 112 (5):744-50 (1999); Piervincenzi R T., et al. *Biosensors & Bioelectronics.* 13(3-4):305-12 (1998); Gill A., et al. *Journal of Biotechnology.* 48(1-2):117-27 (1996); De Jonge, et al. *Molecular Immunology.* 32(17-18):1405-12 (1995); Canaan-Haden L., et al. *Biotechniques.* 19(4):606-8, 610, 612 passim (1995); Graham B M., et al. *Journal of Chemical Technology & Biotechnology.* 63(3):279-89 (1995); Ayala M., et al. *Biotechniques.* 18(5):832, 835-8, 840-2 (1995); U.S. Pat. Nos. 5,648,237, 5,965,456; 5,648,237).

Standard procedures of linking antibodies or antibody fragments to a matrix often utilize the glycan moiety on the antibody for the linkage (see for e.g. U.S. Pat. Nos. 4,937, 183 and 5,635,603). Additional references disclose linkage of antibody fragments to matrixes that are soluble, which reduces the utility of these matrices for diagnostic purposes (see e.g. U.S. Pat. No. 6,410,020; PCT Publication No. WO 98/25971). U.S. Pat. Nos. 6,365,418, 6,329,209, 6,329,209, and 6,406,921 all disclose the linkage of antibodies or antibody fragments to a specific solid support surface by, for example, disulfide linkage.

Selection of Oligonucleotides Linked to Recognition Agents

Several strategies can be exploited in choosing the nucleic acid sequences of the oligonucleotides attached to the oligosaccharide and peptide recognition agents. In the preferred embodiments, the first and second oligonucleotide sequences comprise "primer attachment sites"of at least 5 nucleotides, and in the most preferred embodiment these sites comprise sequences that will not bind the same primers. A "primer" is defined as single stranded length of nucleotides that are complementary to a portion of a nucleotide sequence of interest. Primers can be used as hybridizai:ion probes or as a substrate for the extension of DNA by a polymerase. A "primer attachment site" is that site which the primer will bind to selectively under appropriate conditions. These conditions are known in the art and include, in particular, preferably temperature ranges between 60 and 85° C. In one embodiment, the oligonucleotides comprise non-complementary sequences. In a preferred embodiment, the non-complementary oligonucleotides additionally comprise a sequence that is complementary to one part each of a "linker" oligonucleotide as described below. Additionally the non-complementary oligonucleotides have in one case a free 5' phosphate capable of reacting with a free 3'hydroxyl and in the other case a free 3' hydroxyl.

In a separate preferred embodiment, the oligonucleotides attached to the recognition agents are in part complementary to one another (based on Watson-Crick base pairing). In this embodiment, the two oligonucleotides hybridize to each other. The resulting product can be polymerized using standard DNA polymerases, and the resulting product can be subjected to proximity detection as described herein.

In a further embodiment, the oligonucleotides are attached to a agent that can be covalently linked to one or both of the recognition agents. This reagent could include either streptavidin or biotin, a fluorophore, a reagent with an accessible thiol-reactive group, or any other reagent known in the art to be able to bind either covalently or non-covalently to either the oligosaccharide recognition agent or the peptide recognition agent. In this embodiment, the invention allows use of recognition agents that are not readily linked to oligonucleotides without the requirement of additional adaptor groups, expanding the utility of the invention.

In a separate embodiment, the oligonucleotides are not covalently bound to the recognition agent, but can instead bind via a first affinity reagent. This strategy has advantages, particularly when antibodies are used as the first or second recognition agents. The conjugation of nucleic acid sequences to various antibodies is laborious and may be overcome by making oligonucleotides conjugated to a further reagent with the capacity of binding to the primary antibody, for example in the constant Fe region of a primary binding antibody. In this embodiment, the first and second recognition agents, optionally antibodies, are incubated with the glycoproteins of interest and the oligonucleotides-reagent complexes are added and allowed to preferentially react when in proximity. Methods to identify reagent proximity are outlined herein.

Linkage of Detecting Agents to Oligonucleotides

Adapter groups that are preferred for use in the present invention can be selected for a variety of chemical reasons. An oligonucleotide can be conveniently chosen having a secondary hydroxyl group and/or a primary hydroxyl group with an additional functionality such as an amino, hydroxyl, carboxylic acid, or thiol group. The additional functionality can be used to attach one end of the linker group to the detecting agent by, for example, an amide linkage. The secondary and or primary hydroxyl groups can be used to prepare a dimethoxytrityl or dimethoxytrityl phosphoramidite (a standard method to couple DNA for label attachment, solid-phase immobilization, and formation of hairpin looped structures). This enables the attachment to an oligonucleotide to the 2', 3' or 5'position or a ribosyl group.

Oligonucleotides can be attached through an adaptor moiety to a recognition agent by free 2'-, 3'-, or 5'-hydroxyl group. Such attachments are prepared by, for example, reacting nucleosides bearing at least one free 2'-, 3'-, or 5'-hydroxyl group under basic conditions with a linking moiety having a leaving group such as a terminal L-(CH$_2$)-etc. function, where L is a leaving group. Displacement of the leaving group through nucleophilic attack of, for example, an oxygen anion produces the desired derivative. Leaving groups include but are not limited to halogen, alkylsulfonyl, substituted alkylsul-fonyl, arylsulfonyl, substituted arylsulfonyl, hetercyclcosulfonyl or trichloroacetimidate. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl. After the reagents are contacted, they are crosslinked, to permanently attach them. Suitable crosslinking reagents are known, see, e.g., U.S. Pat. No. 4,542,102 and U.S. Pat. No. 4,713,326, each of which is hereby incorporated herein by reference.

In the case where the recognition agent is an aptamer, oligonucleotide sequences may be attached directly to the aptamer through phosphodiester bonds. In this case, the preferred embodiment of the invention includes additional sequence at the interface to allow flexibility of the oligonucleotide and limit any interference that the oligonucleotide may have with aptamer/ligand interaction.

Further methods to link oligonucleotides to recognition agents comprising peptide sequences include coupling the peptide to a nucleotide and enzymatically incorporating the coupled nucleotide into the oligonucleotide. For example, a peptide can be coupled to the derivatized base, 5-(3-aminoallyl)-uridine triphosphate to produce a peptide-conjugated UTP. The UTP can then be transcribed by an RNA polymerase based on a template to produce an RNA oligonucleotide containing the peptide at every uridine position. This reaction of an oligonucleotide with N-terminal alpha-amino group of a peptide is described in more detail in U.S. Pat. No. 6,083,696, incorporated by reference. In addition, single stranded DNA can be coupled to a peptide chloromethyl ketone. Other methods for coupling non-nucleic acid functional units to nucleic acids may be used. For instance, a peptide could be placed at the 5' or 3' end of RNA. In addition, photo-active bases can be placed at sites in the oligonucleotide, and crosslinked with the recognition agent. Use of directed incorporation could be used also for incorporation of fluorescence tags, biotin, radiolabel, lipid groups, or to cap the oligonucleotide with a uniquely modified base for protection against nuclease digestion.

In one example, an oligonucleotide with 18-atom ethylene glycol moieties and a thiol group at the 3' end can be synthesized by automated techniques known in the art, deprotected by standard methods, and gel purified. Immediately after the deprotection of the 3'-SH group, the oligonucleotide excess DTT is removed and the oligonucleotide is mixed with the peptide linked to chloromethyl ketone and the chloromethyl ketone sulfydryl are allowed to react. The methods described herein do not include all of the schemes for coupling oligonucleotides to non-nucleic acid recognition reagents. However, such methods would be well within the skill of those ordinarily practicing in the art.

Description of Linker Oligonucleotide

In one embodiment of the invention, a "linker" oligonucleotide that is added to the reaction hybridizes to a pair of nearby oligonucleotides and promotes ligation. Ligation will preferentially occur if both the first and second oligonucleotides bind the linker oligonucleotide, because the binding will cause a high local concentration of local first and second oligonucleotides and favour generation of the ligation products derived from dually bound glycoprotein. This mechanism promotes ligation in the presence of the analyte of interest (ie. the peptide glycosylated by specific oligosaccharide structures), improving signal to noise ratio.

In one embodiment of the invention the size of the linker oligonucleotide is variable between two and 100 bases. In the preferred embodiment, a portion of the sequence of the nucleotides in the linker oligonucleotide are complementary (based on Watson-Crick base pairing) to the sequence of the oligonucleotide linked to oligosaccharide recognition agent(s) and an equal portion are complementary to the sequence of the oligonucleotide linked to the peptide recognition agent, and at least 1 base at each end is not complementary to the corresponding sequence of the first or second oligonucleotides.

In a further embodiment, the size of the "linker" oligonucleotide is restricted such that a portion of the sequence of the nucleotide bases in the linker oligonucleotide are complementary to the sequence of the oligonucleotide linked to the oligosaceharide recognition agents and an equal portion are complementary to the sequence of the oligonucleotide linked to the peptide recognition agent and the two sequences abut. Furthermore, at least 1 base at each end is not complementary to the corresponding sequence of the first or second oligonucleotides, and, in a preferred embodiment, each complementary portion is less than 14 bases long. In the most preferred embodiment, the length of each complementary sequence is 10 bases.

In a separate embodiment, the "linker" oligonucleotide is restricted such that a portion of the sequence of the nucleotide bases in the linker oligonucleotide are complementary to the sequence of the oligonucleotide linked to the oligosacoharide recognition agents and another portion are complementary to the sequence of the oligonucleotide linked to the .peptide reccignition agent and the two sequences are separated by at least one oligonucleotide. In a preferred embodiment, each complementary portion is less than 14 bases long. In this embodiment, an additional polymerization step is added before the detection of proximity. In a separate embodiment, the "linker" oligonucleotide is ligated by methods as described in (Baner J. et al., Nucleic Acids Res, 1998, 26:5073-8; Nilsson, et al., Science, 1994, 265:2085-8) to form a circular probe and amplified by "rolling circle amplification."

Care should be taken when designing the "linker" oligonucleotide so that it is not compatible with the oligonucleotide primers to be used by the amplifying enzyme, otherwise a high percentage of resultant product will constitute background. In one embodiment, this problem is overcome by ligating the DNA based oligonucleotides with an RNA oligonucleotide. Because certain polymerases such as Taq DNA polymerase cannot use RNA as a template, no PCR products can arise from this template. An additional modification to reduce the background signal arising from ligated oligonucleotides which have not bound the target may be decreased by adding a competing oligonucleotide. This competing oligonucleotide is designed to be at least in part equivalent to the sequence of one of the first or second oligonucleotides that is complementary to the linker oligonucleotide. However, the competing oligonucleotide does not contain sequences compatible with the oligonucleotide primers to be used in the amplification reaction. The concentration of the competing oligonucleotide should be optimized to the point at which it will readily ligate with the oligonucleotides attached to the recognition agents that are not bound to targets but not compete in ligation with the target bound recognition agent oligonucleotides.

Ligation

After incubation at high concentration of the glycoprotein with the oligosaccharide detecting and peptide recognition agents, a prefered embodiment of the invention provides for the ligation of oligonucleotides linked to the recognition agents.

The ligation reaction is enhanced by proximity of the recognition agents because it is dependent on the statistical probability of two nucleotides being captured by the ligating enzyme. In this invention the ligation can either be dependent on only the probability of interaction due to proximity in solution or dependent on the interaction of the oligonucleotides with complementary DNA sequences in the "linker" oligonucleotide. In the latter embodiment, the ligation is dependent on the hybridization of the first and second oligonucleotides to the "linker"oligonucleotide, in one part complementary to the first oligonucleotide and in a second part complementary to the second oligonucleotide. In these embodiments, the concentration of the first and second oligonucleotide may vary. The concentration dependence is related to the affinity of the recognition agents with their ligand. In addition, in the cases in which either first or second oligonucleotides are partially complementary, or in the case in which a linker oligonucleotide is added, the concentration dependence is also related to the length of overlapping sequence.

In any of these embodiments, DNA ligating enzymes such as T4 DNA ligase can be used. In addition, alternative means to react the conjugated oligonucleotides can be used such as through T4 RNA ligase or chemical ligation. In preferred embodiments, the two oligonucleotides to be ligated are in a conformation such that the 3' end of one oligonucleotide can interact with the 5' end of the other. In one embodiment the oligonucleotides are reacting in the absence of a "linker". In this embodiment, the preferred ligating enzyme can be an RNA ligase such as T4 RNA ligase.

In the preferred embodiment, the contacted recognition agents/glycoprotein complexes are diluted in ligation reaction buffer before ligation to a concentration of recognition agent that will limit non-specific ligation of nucleotides. This ligation reaction buffer contains ATP and ligase enzyme and the detection components required for proximity detection as outlined below. In a preferred embodiment, the concentration to which the components are diluted is approximately $1 \times 10^{-21}$ moles of recognition agent-linked oligonucleotide per 50 microliters of reaction volume. Reactions are most easily carried out at this volume due to current techniques, however this disclosure should not be seen as limiting the volume of the reaction. In each embodiment, the length of ligation and the temperature at which it is carried out may vary, based on standard conditions for the ligating enzyme.

In the case of detecting a target glycoprotein with recognition agents of low affinity and slow binding kinetics a preferred embodiment includes a preincubation with the agents at a sufficiently high concentration for most glycoproteins to be bound. This preincubation is then quickly diluted in a large volume of cold buffer, and a portion of this dilution is subsequently added to a ligation reaction mixture. This ligation reaction mixture contains the template, ATP and ligase enzyme. The ligation mix also contain the detection components as described above. The low temperature minimizes the dissociation of existing complexes while the dilution results in a decrease of the concentration of the oligonucleotides thereby minimizing the background signal.

Analysis of Product

In the preferred embodiments, the proximity of the recognition agents is achieved by detection using real-time PCR. A number of techniques are available to monitor the accumulation of PCR product in real time. In real-time quantitative PCR, the polymerase chain reaction is used to amplify DNA. One preferred embodiment employs intercalating dyes that fluoresce more brightly when bound to double-stranded DNA. In the preferred embodiment, SYBR-green is used to read the presence of double stranded DNA.

In an example, quantification can occur using a sequence detector such as the ABI Model 7700 Sequence Detector™ (Perkin-Elmer PE Biosystems, Foster City, Calif., USA) using a double stranded DNA specific fluorophore such as Sybr Green I™ (Molecular Probes Eugene Oreg. USA), optionally including a non-reactive reference dye such as, for example, 6-carboxy-X-rhodamine. The data can be analyzed using ABI Prism Sequence Detector Software™ (Perkin-Elmer). To confirm that the product of interest is present, gel analysis and sequencing can be performed using standard techniques well known in the art.

A separate embodiment is based on the principles of fluorescent resonance energy transfer (FRET). in a sample in the presence of a non-extendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). By labeling probes with different fluorochromes, several different products can be quantified in a single PCR tube. This is called multiplex PCR and, at present, up to four products can be detected.

Any available monitoring technique may be used. For example, a mechanized sensor such as the Sequence Detection system (ABI Prism, ABD of Perkin Elmer, Foster City, Calif.) which uses a 96-well thermal cycler that can monitor fluorescent spectra in each well continuously in the PCR reaction, may be used. In the Sequence Detection system the PCR reaction contains a fluorescently dual-labeled non-extendible probe that binds to a specific target between the PCR primers. The probe commonly contains a FAM (6-carboxyfluorescein) "reporter dye" on the 5'-end and a TAMRA (6-carboxy-tetramethylrhodamine) "quencher dye" on the 3'-end. When the probe is intact, reporter dye fluorescence emission is quenched by the proximity of the quencher dye. As PCR cycling continues, the hybridized probe is cleaved by the use of a polymerase that contains a 5'-3' nuclease activity. The cleavage of the probe causes the physically separation of the reporter and quencher dyes, resulting in an increase in fluorescence.

Direct Detection of Site Specific Glycosylation

The methods of the present invention can also be carried out by directly detecting proximity effects without ligand binding and amplification as described herein. Thus, for example, an antibody (or other ligand) specific for a target amino acid sequence, and a lectin (or other ligand) specific for a target carbohydrate sequence, could be labeled with interactive detectable moieties from which proximity effects can be observed. Methods of analyzing proximity in this manner include the AlphaScreen homogenous proximity assays descried in Ullman et al. Proc. Natl. Acad. Sci. 91:5426-5430 (1994). In these assays, a light signal is generated when a donor bead and an acceptor bead are brought into proximity. The donor bead contains phthalocyanine, a photosensitizer that generates short-lived singlet oxygen on irradiation at 680 nm. The singlet oxygen species diffuse only a short distance (about 200 nm) before decaying to the ground state. The acceptor beads contain a mixture of chemiluminescer and fluorophores. On reacting with the singlet oxygen species, the chemiluminescer molecules undergo a series of chemical transformations that culminate in a time delayed energy transfer to the fluorophores. The activated fluorophores, in turn, emit an amplified light signal at about 600 nm, resulting in a high signal with very low background.

An alternative method is described by Prestegard et al. in U.S. Publication No. 20020042150 that relies on NMR spectroscopy. The method comprises a) preparing first NMR spectra of a first complex comprising the glycoprotein of interest and a paramagnetically labeled derivative of a first ligand; b) preparing second NMR spectra of a second complex comprising the glycoprotein and a second ligand; and c) analyzing the spectra to determine whether the second ligand binds to the glycoprotein within the paramagnetic zone of the paramagnetically labeled derivative. The first ligand can be targeted at the desired amino acid sequence or the desired carbohydrate sequence. Because paramagnetic labels can perturb (through loss of intensity or line broadening) the peaks on an NMR resonance spectra from nuclei that are within about 20 angstroms of the paramagnetic label, and the level of perturbation is directly correlated to the distance between the paramagnetic label and the nucleus under observation, by forming a complex between the paramagnetically labeled ligand and a glycoprotein of interest, and constructing NMR spectra for the complex, one can identify peaks associated with protons on the second ligand within about 20 angstroms of the paramagnetical label, and calculate the distance from the paramagnetic label to the nuclei on the second ligand.

Comparison of Differential Glycosylation

One utility of the present invention is in the capacity to efficiently compare glycosylation of glycoproteins in disease states with those found in controls and define conditions that could be used as diagnostics in disease. In one aspect therefore, this invention provides a method comparing the proximity of first (oligosaccharide) and second (peptide) recognition agents on proteins derived from independent samples. In the preferred embodiments of this invention these independent samples are derived from at least one tumor cell and at least one control cell.

The comparison between the samples can be achieved by any method known in the art, based on a comparison a first and a second proximity pattern. In this case a first proximity pattern is developed by analyzing glycoproteins from diseased cells, using the methods described herein and the second proximity pattern is prepared from glycoproteins prepared from controls. This pattern is prepared using recognition reagents and may analyze proteins that exhibit selected glycan moieties, analyze glycan moieties that are found on specific proteins, or analyze levels of a particular protein-glycan combination, as described. The levels of proximity may be detected by any method, including binding of radio-, fluorescently-, or chemiluminescently-labeled probes, or analysis of product formation by intercalating dyes, or by formation of secondary reaction product when the proximity, for example, allows catalysis of a secondary reaction. In one preferred embodiment, the comparison is achieved by comparing signals from RT-PCR (as described above). Because RT-PCR allows quantification of signals, this embodiment provides the most diagnostic tools. Signals can be compared using automated systems as outlined in (Morrison et al., 1998, *Biotechniques* 24:954-962.). Statistical comparisons based on product present can be performed using standard tests.

The present invention may be embodied in other specific forms without departing from the spirit or essential attributes thereof and accordingly reference should be made to the appended claims rather than the foregoing specifications as indicating the scope of the invention.

DEFINITIONS

"PCR primer nucleotide sequence" refers to a defined sequence of nucleotides forming an oligonucleotide that is used to anneal to a homologous or closely related sequence in order form the double strand required to initiate elongation using a polymerase enzyme.

"Amplifying" means duplicating a sequence one or more times.

The term "nucleic acid" or "oligonucleotide" means a polynucleotide such as deoxyribonucleic acid (DNA) or ribonucleic acid (RNA).

"Complementary oligonucleotides" are defined as two chains of polynucleotides which have the capacity to bind via traditional Watson-Crick base pairing.

The term "oligosaccharide" refers to polymers of monosaccharides that can be linear or branched. Oligosaccharides include modifications of monosaccharides.

"Glycoprotein" refers to any protein in which one or more carbohydrate units have been attached covalently to the protein by posttranslational processing.

"Detergent" is defined as a surface-active agent (surfactants) containing a hydrophobic portion, which is more soluble in oil-like solutions, and a hydrophilic portion, which is soluble in water.

"Differential glycosylation" refers to an increased, upregulated or present, or decreased, downregulated or absent, glycosylation of proteins glycoproteins in diseased versus normal tissue or cells. "Differential expression" refers to an increased or decreased protein expression in a sample.

A "control" is an alternative subject or sample used in an experiment for comparison purposes.

REFERENCES

U.S. Pat. No. 6,203,999 Robbins, et al. Mar. 20, 2001 Detection of prostate and other cancers by assaying for cancer-specific antigens having linked oligosaccharides which are at least triantennary.

U.S. Pat. No. 4,542,102 Dattagupta N.; Crothers, D. M. Sep. 17, 1985 Coupling of nucleic acids to solid support by photochemical methods U.S. Pat. No. 4,713,326 Dattagupta, et al. Dec. 15, 1987 Coupling of nucleic acids to solid support by photochemical methods U.S. Pat. No. 6,261,791 Reiter, et al. Jul. 17, 2001 Method for diagnosing cancer using specific PSCA antibodies U.S. Pat. No. 6,077,951 Redmond, et al. Jun. 20, 2000 Glycosylhydrazines preparation immobilization and reactions of glycoprotein analysis and O-glycan removal E.P. 1008852A1 Römisch, J ürgen Dr.; Feussner, Annette; Process for the specific detection of glycosylated proteins E.P. 0832431B1: Landegren, Ulf; Immunoassay and kit with two reagents that are cross-linked if they adhere to an analyte U.S. 20020051974A1: Dodge, A. H., Meng, Y. G., Sims, P. W., Sinicropi, D. V., Williams, P. M., Wong, W. L. PCR ASSAY U.S. 20020064779A1: Landegren, U.; Fredriksson, S, Methods and kits for proximity probing U.S. Pat. No. 5,660,985: Pieken, W., Tasset, D., Janjic, N., Gold, L., Kirschenheuter, G. P.; High affinity nucleic acid ligands containing modified nucleotides Apr. 27, 1995

U.S. Pat. No. 6,083,696: Biesecker, G., Jayasena, S. D., Gold, L., Smith, D., Kirschenheuter, G.; Systematic evolution of ligands exponential enrichment: blended selex Oct. 23, 1997

U.S. Pat. No. 5,817,785: Gold, L., Tuerk, C.; Methods of producing nucleic acid ligands Nov. 13, 1996

U.S. Pat. No. 5,648,214: Nieuwlandt, D. T., Gold, L., Wecker, M.; High-affinity oligonucleotide ligands to the tachykinin substance P Sep. 9, 1994

Baner J, Nilsson M, Mendel-Hartvig M, Landegren U, Signal amplification of padlock probes by rolling circle replication, Nucleic Acids Res 1998 Nov. 15;26(22): 5073-8.

Belanger et al., Molecular mass and carbohydrate structure of prostate specific antigen: studies for establishment of an international PSA standard, Prostate 27(4):187-197 (1995).

Drickamer, K., J. Biol. Chem., 1988, 263, 9557;

Drickamer, K., Curr. Opin. Struc. Biol., 1993, 3, 393;

Drickamer, K., Biochemical Society Transactions, 1993, 21, 456

Endo T. (1996) Fractionation of glycoprotein-derived oligosaccharides by affinity chromatography using immobilized lectin columns Journal of *Chromatography. A* 720 (1-2):251-61.

Gibson, U. E., heid, C. A., Williams, P. M. Genome Res., 6, 995-1001

Harlow and Lane (1988) Antibodies: A Laboratory Manual, Cold Spring Harbor Laboratory Press.

Huse et al. (1989) Science 246:1275-1281

Kwiatkowski R W, Lyamichev V, de Arruda M, Neri B, Clinical, Genetic, and Pharmacogenetic Applications of the Invader Assay., Mol Diagn 1999 December;4(4):353-364

Litynska, A., Przybyoto M., Pochec E., Hoja-Lukowicz D, Ciolczyk D., Laidler P., Gil D. Comparison of the lectin-binding pattern in different human melanoma cell lines. Melanoma Rsch. 2001. 11:205-212.

Merrifield (1986) Science 232:341-347

Morrison T B, Weis J J, Wittwer C T. Quantification of low copy transcripts by continuous SYBR Green I monitoring during amplification. Biotechniques 1998;24:954-958, 960, 962

Nadeau J G, Pitner J B, Linn C P, Schram J L, Dean C H, Nycz C M, Real-Time, Sequence-Specific Detection of Nucleic Acids during Strand Displacement Amplification. Anal Biochem 1999 Dec. 15;276(2):177-187

Nilsson M, Malmgren H, Samiotaki M, Kwiatkowski M, Chowdhary B P, Landegren U, Padlock probes: circularizing oligonucleotides for localized DNA detection, Science 1994 Sep. 30;265(5181):2085-8

Russell and Barton, "Structural features can be unconserved in proteins with similar folds," J. Mol. Biol. 244:332-350, 1994. (19 pages)

Steuerwald N, Cohen J, Herrera R J, Brenner C A, Analysis of gene expression in simple oocytes and embryos by real-time rapid cycle fluorescence monitored RT-PCR- .Mol iium Reprod 1999 November;5(11):1034-9

Tyagi, S. Kramer, F. R. Molecular beacons: probes that fluoresce upon hybridization, Nat Biotechnol (1996), 14, 3, 303-8

Van Deursen P B, Gunther A W, van Riel C C, van der Eijnden M M, Vos H L, van Gemen B, van Strijp D A, Tackent N M, Bertina R M, A novel quantitative multiplex NASBA method: application to measuring tissue factor and CD14 mrna levels in human monocytes. Nucleic Acids Res 1999 Sep. 1;27(17):e15

Vieira-Breitwieser O, Schwarz-Herzke B, Schmitz B., Doerfler W., Interactions of plant lectins with DNA. 20th Annual International Lectin Meeting Abstracts, T25, 2002

Wells and Peitsch, "The chemokine information source: identification and characterization of novel chemokines using the worldwideweb and expressed sequence tag databases," Journal of Leukocyte Biology 61:545-550 May 1997. (6 pages)

White S R, et al., Signal amplification system for DNA hybridization assays based on in vitro expression of a DNA label encoding apoaequorin, Nucleic Acids Res. 1999 Oct. 1;27(19):e25

I claim:

1. A method of detecting oligosaccharide sequences on glycoproteins of interest comprising:
   a) providing a glycoprotein;
   b) contacting said glycoprotein with a first recognition agent for detecting one or more oligosaccharides on said glycoprotein and a second recognition agent for detecting one or more peptides on said glycoprotein; and
   c) detecting proximity of said first and second recognition agents.

2. The method as in claim 1 wherein: said first recognition agent is linked to a first oligonucleotide comprising a first sequence and said second recognition agent is linked to a second oligonucleotide comprising a second sequence.

3. The method as in claim 2 wherein said first and second sequences are not complementary and additionally comprising:
   i) contacting a third oligonucleotide, defined as the "linker" oligonucleotide, comprising a third sequence in a first part complementary to said first sequence and in a second part complementary to said second sequence, forming a mixture;
   ii) incubating said mixture with a reagent capable of ligating said complementary oligonucleotide sequences, forming a ligated mixture; and
   iii) detecting proximity of said first and second recognition agents.

4. The method as in claim 3 wherein said complementary sequences are each less than 14 base pairs long.

5. The method as in claim 1 wherein proximity is defined as within a distance less than the size of the glycoprotein when folded in its natural conformation.

6. The method as in claim 3 wherein said method of detecting proximity comprises:
   a) contacting said ligated mixture with a fourth oligonucleotide comprising a fourth sequence complementary to a part of said first sequence and a fifth oligonucleotide comprising a fifth sequence, complementary to a part of said second sequence, forming a PCR mixture;
   b) subjecting said PCR mixture to amplification of DNA between said fourth and fifth sequences; and
   c) detecting amplified DNA.

7. The method as in claim 6 wherein said amplified DNA is detected using real-time PCR monitoring.

8. The method as in claim 1 wherein the first recognition agent detects a single type of oligosaccharide moiety and said second recognition agent detects a plurality of peptide structures.

9. The method as in claim 6 wherein:
   a) a binding site of said second recognition agent to said oligosaccharide is known;
   b) the length of said first and said second oligonucleotides are varied in sequential reactions;
   c) the detection of amplified DNA is compared for said sequential reactions; and
   d) the size of the distance between recognition agents correlating with said variations in oligonucleotide length is compared to protein structures or protein structure models to infer location of the binding site of said first recognition agent.

10. The method as in claim 1 wherein said second recognition agent is a mixture of aptamers.

11. The method as in claim 1 wherein said first recognition agent detects a plurality of oligosaccharide moieties and said second recognition agent reacts with a single peptide sequence.

12. The method as in claim 1 wherein the first recognition agent comprises a lectin.

13. The method as in claim 1 wherein said second recognition agent detects a peptide sequence.

14. The method as in claim 1 wherein said second recognition agent detects a protein structure.

15. The method as in claim 1 wherein said first recognition agent or said second recognition agent or both recognition agents comprise at least one antibody.

16. The method as in claim 1 wherein said first recognition agent or said second recognition agent or both recognition agents are at least one aptamer.

17. The method as in claim 1 wherein said glycoprotein is found in a disease state.

18. The method as in claim 1 wherein said glycoprotein is derived from a cell lysate.

19. The method as in claim 1 wherein said glycoprotein is found in serum.

20. The method as in claim 1 further comprising comparing said proximity of said first and second recognition agents on said glycoprotein derived from independent samples.

21. The method as in claim 20 wherein said independent samples are derived from at least one tumor cell and at least one control cell.

22. The method as in claim 20 wherein said comparison is achieved by comparxng signals from RT-PCR.

23. The method as in claim 1 wherein either said first recognition agent or said second recognition agent is additionally bound to a solid matrix.

24. The method as in claim 2 wherein said oligonucleotide sequences are in one part complementary to each other and in another part, adjacent to said linkage with said recognition agents, not complementary and further comprising:
   a) incubating said recognition agents with a reagent capable of ligating said complementary oligonucleotide sequences, forming a ligated mixture;
   b) detecting proximity of said first and second recognition agents.

25. The method as in claim 24 wherein said method of detecting proximity comprises:
   a) contacting said ligated mixture with a third oligonucleotide comprising a third sequence complementary to a part of said first sequence and a fourth oligonucleotide comprising a fourth sequence, complementary to a part of said second sequence, forming a PCR mixture;
   b) subjecting said PCR mixture to amplification of DNA; and
   c) detecting amplified DNA.

26. The method as in claim 2 wherein said sequences comprise complementary base pairs and additionally comprising reacting the agents with an enzyme to polymerize DNA.

27. A method of detecting oligosaccharide sequences on glycoproteins of interest comprising:
   a) providing a glycoprotein;
   b) contacting said glycoprotein with a first recognition agent linked to a first oligonucleotide comprising a first sequence for detecting one or more oligosaccharides on said glycoprotein, thereby binding said first oligonucleotide to said glycoprotein;
   c) subjecting said bound first oligonucleotide to PCR amplification; and
   d) detecting amplified DNA.

* * * * *